United States Patent [19]

Harrison, Jr. et al.

[11] Patent Number: 4,956,290

[45] Date of Patent: Sep. 11, 1990

[54] LARGE SCALE PROCESS FOR THE PURIFICATION OF ALCOHOL OXIDASE

[75] Inventors: Roger G. Harrison, Jr., Norman; Lynn P. Nelles, Bartlesville, both of Okla.

[73] Assignee: Phillips Petroleum Company, Bartlesville, Okla.

[21] Appl. No.: 331,220

[22] Filed: Mar. 27, 1989

[51] Int. Cl.$^5$ .......................... C12N 9/04; C12N 9/02; C12R 1/84; C12Q 1/26

[52] U.S. Cl. .................................... 435/189; 435/25; 435/147; 435/168; 435/188; 435/190; 435/259; 435/803; 435/815; 435/816; 435/938

[58] Field of Search ................. 435/25, 147, 168, 188, 435/189, 190, 259, 938, 171, 803, 814, 815, 816

[56] References Cited

U.S. PATENT DOCUMENTS

| | | | |
|---|---|---|---|
| 4,250,261 | 2/1981 | Eggeling et al. | 435/190 |
| 4,540,668 | 9/1985 | Hopkins | 435/190 |
| 4,619,898 | 10/1988 | Hopkins | 435/190 |
| 4,729,956 | 3/1988 | Hopkins | 435/188 |
| 4,751,003 | 6/1988 | Raehse et al. | 435/814 |
| 4,795,709 | 1/1989 | Hopkins | 435/189 |

OTHER PUBLICATIONS

*Biotechnology Letters* 6,621 (1984), Vaks, "A Semi-Continuous Process for the Production of Human Interferon-αc from *E. coli* Using Tangential Flow Microfiltration and Immuno-Affinity Chromatography".

*Process Biochemistry*, Feb. 1985, p. 26, Le "Crossflow Microfiltration for Recovery of Intracellular Products".

*Process Biochemistry*, Apr. 1984, p. 67, Kroner, "Cross-Flow Filtration in the Downstream Processing of Enzymes".

*ASM News*, 50,299 (1984), Gabler, "Tangential Flow Filtration for Processing Cells, Proteins, and Other Biological Components".

*Biotech & Bioengineering*, 28,422 (1986), Devereux, "Membrane Separation of Protein Precipitates: Studies with Cross Flow in Hollow Fibers".

*Enzyme Microb. Technol.*, 6,201 (1984), Quirk, "Investigation of the Parameters Affecting the Separation of Bacterial Enzyme from Cell Debris by Tangential Flow Filtration".

*The Chemical Engineer*, Jun. 1984, p. 10, Bertera, "Development Studies of Crossflow Microfiltration".

*Biotechnology Letters*, 7,471 (1985), Datar, "Studies on the Separation of Intracellular Soluble Enzymes from Bacterial Cell Debris by Tangential Flow Membrane Filtration".

*Biotechnical Letters*, 5,277 (1983), Quirk, "Tangential Flow Filtration A New Method for the Separation of Bacterial Enzymes from Cell Debris".

Primary Examiner—Herbert J. Lilling
Attorney, Agent, or Firm—Richmond, Phillips, Hitchcock, & Umphlett

[57] ABSTRACT

A process for the purification of alcohol oxidase from whole cells of *Pichia pastoris* grown on methanol by the sequential steps of autolysis, crossflow filtration, ultrafiltration and recrystallization.

19 Claims, No Drawings

LARGE SCALE PROCESS FOR THE PURIFICATION OF ALCOHOL OXIDASE

FIELD OF THE INVENTION

This invention relates to the large scale purification of enzymes.

Background

Scaling up enzyme purification and recovery methods for large scale production is often very difficult. Many of the processes which are practical in small scale enzyme preparations are impractical, uneconomical, and too labor-intensive for large scale production.

For example, it is known that alcohol oxidase can be recovered from *Pichia pastoris* grown on methanol. In small scale preparations, alcohol oxidase is recovered by homogenizing *Pichia pastoris* cells grown at high cell density (85-150 grams of biomass dry weight per liter) by bead milling followed by filtration or centrifugation to remove cell solids, yielding a crude solution containing alcohol oxidase. The crude solution is then dialyzed or ultrafiltered with a final ionic concentration of between 0.05M and 0.01M and a pH of from about 5.75 to about 6.75 to yield crystalline alcohol oxidase. However, this process is only suitable for small scale preparation with a beginning volume of about 10 liters.

To scale up this small scale alcohol oxidase preparation, a number of difficulties must be overcome. First, *Pichia pastoris* is preferably grown at high cell densities between 85-150 grams of biomass dry weight per liter. This cell density may not be suitable for some processing steps, but it is desirable to maintain because of the higher initial concentration of alcohol oxidase it may provide. This higher initial concentration of alcohol oxidase, if maintained, may result in higher yields and lower volumes of material to process. Second, since alcohol oxidase is a large enzyme, being approximately 650,000 daltons in size, there is very little literature guidance as to what operating parameters may be appropriate for an enzyme of this size. Further, the literature appears to indicate that filtration, such as crossflow filtration, may provide low yields of an enzyme of alcohol oxidase's size. Finally, scaling up the preparation of alcohol oxidase must be controlled so that acceptable purity, yield, and specific activity of the alcohol oxidase can be obtained.

Thus, it would be a significant contribution to the art to develop a large scale process for the purification of alcohol oxidase in high purity.

Further, it would be advantageous if the large scale process for the purification of alcohol oxidase utilized conventional large scale filtration devices while providing high alcohol oxidase yields.

Additionally, it would be advantageous if the specific activity of the alcohol oxidase purified on large scale remained at levels as high as those obtained from small scale purification preparations.

Thus, it is an object of the present invention to provide a large scale process for the purification of alcohol oxidase of high purity.

It is a further object of the present invention to provide a large scale process for the purification of alcohol oxidase in high yield utilizing conventional large scale filtration devices.

It is another object of the present invention to provide a process to purify alcohol oxidase while maintaining high levels of alcohol oxidase specific activity.

Other aspects, objects, and several advantages of this invention will be apparent from the specification, examples, and claims.

Summary of the Invention

In accordance with the present invention we have discovered a process for the purification of alcohol oxidase from whole cells of *Pichia pastoris* grown on methanol comprising the steps of:
  (a) forming an aqueous suspension of from about 0.8 to about 6 volume percent of an autolytic treating agent, and a quantity of said whole cells of *Pichia pastoris* containing alcohol oxidase, wherein said cells are present in an amount in the range of from about 85 to about 150 grams per liter of said aqueous suspension, in a manner whereby said whole cells release at least a portion of said alcohol oxidase thereby forming an aqueous liquor;
  (b) filtering said aqueous liquor by crossflow filtration to separate at least a portion of said alcohol oxidase from said aqueous liquor thereby forming an alcohol oxidase solution;
  (c) ultrafiltering and desalting said alcohol oxidase solution to form an alcohol oxidase suspension; and
  (d) recrystallizing alcohol oxidase from said alcohol oxidase

Detailed Description of the Invention

According to the present invention, *Pichia pastoris* is cultured under aerobic aqueous fermentation conditions using methanol or a combination of methanol and other selected organic compounds as the carbon and energy source. Preferably the methanol is supplied under conditions such that methanol is the growth-limiting factor. Most preferably, the *Pichia pastoris* will be grown to the desired density on a readily available carbon source including, but not limited to, glucose and then grown for a suitable period of time on methanol limiting conditions to obtain high concentrations of alcohol oxidase in the *Pichia pastoris* cells. The methanol limiting conditions are defined for purposes of this disclosure as a concentration of methanol which is the minimal concentration which results in a maximum growth rate for a given set of fermentation culture conditions. *Pichia pastoris* is preferably cultured under these conditions to obtain alcohol oxidase accumulation in the *Pichia pastoris* cells. Preferably fermentation is conducted under high cell density conditions, i.e., so that cell density ranges from about 85 to 150 grams on a dry weight basis per liter of ferment. *Pichia pastoris* is grown in a batch or continuous process in the presence of oxygen, methanol, and an assimilable source of nitrogen. Various types of fermentation processes and apparatuses known in the art can be utilized. For example, a foam-type fermenter such as described in U.S. Pat. No. 3,982,998, or other suitable fermenter can be used.

Oxygen can be supplied to the fermenter as such, or in the form of air or oxygen-enriched air, in a range of pressures from such as about 0.1 atm to about 100 atm, as is known in the art. The assimilable source of nitrogen for the fermentation can be any organic or inorganic nitrogen containing compound which provides nitrogen in a form suitable for metabolic utilization by the microorganisms. Suitable organic nitrogen sources include, for example, proteins, amino acids, urea, and the like. Suitable inorganic nitrogen sources include, for example, ammonia, ammonium hydroxide, ammonium nitrate, and the like. The presently preferred nitrogen sources include ammonia and ammonium hydroxide for convenience and availability.

The pH range in the aqueous *Pichia pastoris* ferment should be in the range of from about 3.5 to about 5.5. Preferably pH range for the growth of *Pichia pastoris* is dependent to some extent on the medium employed, as well as on the particular strain, and thus may change somewhat with a change in medium as can be readily determined by those skilled in the art.

Sufficient water is maintained in the fermentation medium so as to provide for the particular requirements of the *Pichia pastoris* strain employed as well as to provide a carrier fluid for water soluble nutrients. Minerals, growth factors, vitamins, and the like, generally are added in amounts which vary according to the strain of *Pichia pastoris* utilized and the selected culture conditions, and are known to those skilled in the art or are readily determined by them.

The growth of *Pichia pastoris* is sensitive to the operating temperature of the fermenter and each particular strain of *Pichia pastoris* has an optimum temperature for growth. Exemplary fermentation temperatures are in the range of from about 20° C. to about 35° C. The temperature selected will generally depend upon the strain employed in the process since each one will have a somewhat different temperature/growth rate relationship.

Fermentation pressures are generally within the range of from about 0.1 to about 100 atmospheres, more usually about 1 to about 30 atmospheres, and more preferably about 1 to about 5 atmospheres since the higher pressures result in a greater level of dissolved oxygen in the aqueous medium and usually higher cell productivities.

Alcohol Oxidase Isolation

A fluid is prepared which is a suspension containing cells of *Pichia pastoris*. The suspension can be fermenter effluent which can be used directly, or preferably after adjusting the pH as described below. Alternatively the suspended *Pichia pastoris* cells can be initially separated from the fermentation medium, for example, by centrifugation or by filtration through filters having a pore size less than the size of the individual cells, and subsequently resuspended in a convenient volume of water or of an appropriate aqueous buffer, for example $KH_2PO_4/K_2HPO_4$ buffer at 0.2 M. Satisfactory results are obtained if the fluid cell density is greater than about 85 grams on a dry weight basis per liter of fluids. In addition satisfactory results are obtained if the fermenter effluent, where it is to be used as the fluid, is first adjusted to a pH between 7.5-8.5 by the addition of a base such as ammonium hydroxide, sodium hydroxide, and the like. The pH of the suspension needs to be adjusted prior to autolysis. However, it is considered preferable to adjust the pH broadly in the range of about 6–10 since in this range the enzyme is active and stable. Preferably the pH of the suspension will be maintained between about 7.5 to about 8.5.

In any event, the *Pichia pastoris* cells produced by fermentation should be preferably utilized immediately after fermentation on methanol to minimize alcohol oxidase degradation. Less preferably the *Pichia pastoris* cells containing the alcohol oxidase may be stored at approximately 4° C. preferably with a bacteriostatic agent including, but not limited to, sodium azide until used. Since alcohol oxidase concentrations in *Pichia pastoris* appear stable under these conditions, it appears that alcohol oxidase can be extracted from these cells for up to several months following their growth.

The *Pichia pastoris* cells should be admixed with an autolytic treating agent component to form an aqueous suspension which should generally contain from about 85 to about 150, preferably from about 100 to about 130, grams of cells per liter. Lower cell concentrations can be employed, though results may not be as satisfactory. Present data indicate that, at cell concentrations as low as 2 to 3 weight percent, enzyme release does not occur. It is most preferred to use undiluted fermenter effluent.

The remaining percentage of the aqueous suspension is essentially water and the autolytic treating agent. The water component can be pure water, water containing dilute salts or the natural liquor of the fermenter effluent as may be convenient, available, or desired.

The autolytic treating agents employed can be generally termed polychloro derivatives of non-benzenoid hydrocarbons or ethers. More particularly, these autolytic treating agents are polychloro derivatives of alkanes, and ethers which are normally liquid at standard temperatures and pressure.

Among the polychloro derivatives of alkanes and ethers which can be employed, and which compounds are liquid at normal temperature and pressure, are the following examples which can be used alone or in admixture, and which are intended to be illustrative and not necessarily selected from the group consisting of
diethyl ether
methylene chloride,
1,2-dichloroethylene (cis or trans),
ethylidene chloride,
chloroform,
2,2-dichloropropane,
1,1,1-trichloroethane,
carbon tetrachloride,
ethylene chloride,
trichloroethylene,
propylene chloride,
1,1,2-trichloroethane,
tetrachloroethylene,
trimethylene chloride,
s-tetrachloroethane,
1,2,3-trichloropropane, and
pentachloroethane.

Presently preferred are chloroform, methylene chloride, or diethyl ether.

Based on the total of the three-component system of *Pichia pastoris* cells, water and autolytic treating agent, the amount of autolytic treating agent should be that amount which is effective to achieve autolysis of the particular cells with the agent chosen and the time and temperature employed. Suggested is a general range of from about 0.8 to about 6, and preferably from about 1.0 to about 5 volume percent autolytic treating agent. The optimum amount of autolytic treating agent used depend on the particular agent utilized.

Admixing of the three-component system can be by any convenient manner, such as pouring together, stirring, and the like, depending on the quantities and materials to be employed. There is no need for physical beating or violent admixing as to cause physical rupture of cells.

Any order of admixing is suitable. Mixing the fermenter effluent with the autolytic treating agent, presently is preferred. However, the autolytic treating agent and water component can be admixed first, and the *Pichia pastoris* cells then added thereto.

The temperature of contacting the three components can be any temperature which is convenient, such as substantially room temperature, or the temperature of the fermenter effluent as it normally comes from the fermenter when the fermenter effluent is to be directly employed. Usually, the aqueous suspension is incubate at a temperature range of from about 10° to about 35° C., more preferably the temperature range of from about 25° to about 35° C., is employed. Conveniently, and preferably, the contacting temperature is that temperature employed for holding or incubation.

The "holding" time or "incubation" time should be a time of at least about 16 hours, more usually a time in the range of from about 16 to about 90 hours. Presently preferred is an incubation time of about 26 hours at 32° C. or about 72 hours at 25° C.

The three-component system, *Pichia pastoris* cells, water, and autolytic treating agent, in admixture or aqueous suspension, can be maintained in a suitable holding vessel or tank which can be stainless steel, glass-lined, or similar construction, for the desired time. The fermentation vessel itself can be used as the holding vessel. The pH should be maintained as in the range :rom about pH 7 to about pH 9. Normally, continuous stirring is not required, though a mild stirring of the admixture can be employed, if desired.

There is no presently known necessity to shield the contents from air or oxygen, though a tightly closed container is important to minimize loss of the autolytic treating agent from the vessel.

There is no presently known necessity to shield the contents from light, though normally the contents of the holding vessel are maintained in darkness.

During the holding time or incubation period, a significant portion of the alcohol oxidase present in the *Pichia pastoris* cells will be released, forming an aqueous liquor.

The aqueous liquor should then be filtered by crossflow or tangential flow filtration in which the aqueous liquor permeates through the filter medium at right angles to the direction of flow of the aqueous liquor. Crossflow filtration is preferably performed with a filter medium having pore sizes generally ranging from about 0.1 $\mu$m to about 5 $\mu$m and more preferably about 1 $\mu$m. The filter medium may be made from many materials including, but not limited to, ceramic or polymeric materials; currently preferred are $Al_2O_3$ ceramic materials for ease of cleaning and high permeate flow rates.

The superficial velocity (volumetric flow rate divided by the cross section area) should be maintained at a velocity sufficient to minimize filter blockage due to debris accumulating on the filter's surface. Superficial velocities generally ranging from about 5 feet per second to about 70 feet per second are currently preferred with a superficial velocity of about 30 feet Per second being most preferred.

The size of filter should be selected to provide a filter of adequate size to allow quick processing but minimize the amount of alcohol oxidase lost by filter retention.

Surprisingly, it has been found that no dilution is necessary for cross flow filtration when autolysis is used to extract alcohol oxidase from *Pichia pastoris* although dilution with water or buffer increases volumetric passage of aqueous liquor through the filter medium as a result of decreased debris and proteins accumulation on the filter medium surface.

It is recommended that the crossflow filter be subjecting to backflushing or backpulsing at intervals to clear debris built up on the filter. The intervals of backflushing or backpulsing will vary depending on the cell concentration, superficial velocity, pressure, and nature of the debris present, and can readily be determined by one skilled in the art.

As aqueous liquor (containing alcohol oxidase) passes through the crossflow filter, the cell debris concentration in the aqueous liquor will increase as the permeate containing alcohol oxidase is extracted. If left unchecked this would result in lowered passage of alcohol oxidase through the filter. Additional liquid, such as water in a buffer solution may be added to the aqueous liquor intermittently as required to reverse the effects of this concentration. Preferably, the additional liquid will be added by backpulsing. The total water added should range from from about 2 to about 4 times the original volume of aqueous liquor and preferably about 3 times the original volume.

Crossflow filtration should generally be performed at a temperature range from about 4° C. to about 20° C. and preferably from about 13° C. to about 15° C.

The permeate from crossflow filtration discussed above will provide an alcohol oxidase solution which may be further processed to concentrate and desalt the solution to facilitate the crystallization of the alcohol oxidase.

The preferred method of concentration and desalting is to perform crossflow ultrafiltration on the alcohol oxidase solution. Ultrafiltration is performed by utilizing a filter medium having a molecular weight cut-off ranging from about 10,000 MW to about 500,000 MW. Preferably the molecular weight cut-off will be about 100,000 MW. The superficial velocity at which the crossflow ultrafiltration is performed should be sufficient to minimize filter blockage due to polarization concentration effect caused by the presence of proteins and other biological components on the filter medium surface. Preferably the initial superficial velocity of the alcohol oxidase solution will be of sufficient velocity to provide turbulent flow through at least a portion of the filter. The size of the ultrafiltration unit depends on the volume of alcohol oxidase solution being processes and may readily be determined by one skilled in the art.

The temperature at which concentration and desalting by crossflow ultrafiltration is performed should generally range from about 4° C. to about 20° C. and most preferably the temperature will be about 7° C.

For optimum recrystallization it is preferred that the ending conductivity of the desalted and concentrated alcohol oxidase generally range from about 500 $\mu$mho/cm to about 4,000 $\mu$mho/cm, and more preferably the conductivity should range from about 1,900 $\mu$mho/cm to about 2,500 $\mu$mho/cm.

Crystallization of the alcohol! oxidase solution is performed by adjusting the pH of the alcohol oxidase solution from 6.0 to about 7.0 and preferably about pH 6.3. The solution is then allowed to stand for a period of time generally in the range of about 9 hour to about 72 hours and preferably in the range of from about 16 hours to about 24 hours.

The temperature at which the crystallization occurs can be maintained, generally in the range of from about 2° C. to about 25° C. and preferably in the range of from about 4° C. to about 10° C.

Optionally the alcohol oxidase crystals may be stirred and recovered from the remaining liquid by centrifugation, Preferably utilizing a centrifuge at a ran&e of from about 1,000 x g to about 4,000 x g for a period of time ranging from about 5 to about 10 min. sufficient to separate the liquid from the crystals.

The following non-limiting examples are provided to further illustrate the practice of the present invention.

Examples

Strains

*Pichia pastoris* NRRL-11430.

Background Information for Examples

All of the procedures were performed with *Pichia pastoris* high-cell-density broth (120–150 g/1 dry solids basis), produced either by a 15-liter LSL Biolafitte fermenter (Princeton, N.J.) or a 400-liter New Brunswick Scientific fermenter (Edison, N.J.). Preparation of this broth using methanol as the carbon source has been described in Shay et al., *Journal of industrial Microbiology* 2, 79 (1987). All of the broths I5 were stored at 4° C. and used within four days of harvesting from the fermenter.

Relative salt concentrations were monitored with a Chemtrix conductivity meter (type 700, Hillsboro, Oreg.).

Example I

Purification of Alcohol Oxidase 10 liters of high-cell-density *Pichia pastoris* broth to which 0.02 $NaN_3$ had been added was removed from 4° C. storage.

The pH of the broth was adjusted to 8.25 with concentrated $NH_4OH$. Methylene chloride was then stirred in to 1% volume per volume (v/v) concentration, and the solution was incubated at 32° C. for 24 hours in tightly sealed 2 and 4 liter polyethylene jars.

9 liters of the resulting broth was diluted to 13 liters with filtered deionized (DI) water.

The diluted broth was then crossflow filtered on a Norton Caraflo microfiltration system with a 10 $\mu m$ pore size and a 1.0 $ft^2$ total filtration area. Broth was recirculated through the system at a rate of 95 liters/minute. The steady state temperature of the recirculating broth was ranged from 4°–8° C. Permeate was collected in a 50 liter vat equipped with a MeOH/water cooling jacket.

Backpulsing was conducted at approximately 30 minute intervals with sufficient filtered Dl water to return the total volume of the broth to the 13 liter level. During this time, the permeate rate typically varied between 60 ml/min immediately before a backpulse to 180 ml/min immediately after a backpulse. Filtration was stopped when a total of 27 liters of permeate had been collected, containing 864,000 units of alcohol oxidase activity. This corresponds to the recovery of 96 units/ml of the 9 liters of broth filtered.

By comparison, the remaining 1 liter (out of the original 10 liters that was autolytically lysed) was centrifuged at ~20,000 x g. The supernatant contained 110,500 units, which corresponds to the recovery of 110 units/ml of broth.

Using an Amicon 100 K NMW cut-off hollow fiber cartridge, the 27 liters were concentrated to ~6.5 liters. Filtered DI water was then added to the concentrate intermittently as filtration continued on the hollow fiber cartridge. The total volume of water added was sufficient to lower the conductivity of the concentrate to ~2500 $\mu mho/cm$. No more water was added and the volume of the concentrate was brought down to 4.5 liters by continued processing with the Amicon cartridge. The pH of the final concentrate was 7.Z at this stage and it was lowered to 6.3 by stirring in sufficient 1N $H_3PO_4$ and held overnight (~17 hours) at 4° C. The crystals were harvested by centrifugation for 10 minutes at 2,000 x g on an RC-5B centrifuge. The crystals were washed twice by resuspension in 0.05 M potassium phosphate (pH 7.5) and centrifugation as above. The crystals were dissolved in DI water and particulate material removed by centrifugation as above. Solid sucrose to 60% (w/v) was added. A 46% yield of alcohol oxidase activity present in the 9 liters of broth was obtained. Taking in to account, the alcohol oxidase in the final concentrate which did not crystallize, 82% of the activity present in the 9 liters of broth was present in the final concentrate prior to crystallization. A specific activity of 36.7 units/mg protein was obtained and purity was found to be >97% by high performance gel permeation chromatograph (GP-HPLC).

This example demonstrates that the purification of alcohol oxidase by the present simple process provides high yields, high purity and high specific activity.

Example II

Purification of Alcohol Oxidase

(Pilot Plant Scale)

46 liters of high-cell-density *Pichia pastoris* broth was held at 10°–12° C. in a 100 liter jacket vat. Solid sodium azide was added to a final concentration of 0.02% (w/v). The pH (initially at 5.26) was adjusted to 8.39 with concentrated $NH_4OH$ and 460 mls of methylene chloride were added with stirring. The vat was tightly sealed and warm water circulated through the jacket to bring the contents to 34° C. Warm water circulation was stopped (but jacket was not drained) and the vat allowed to stand for ~25 hours without stirring.

20 liters of filtered DI water was added and crossflow filtration initiated using 3–1.5 square feet Norton Ceraflo filters in parallel.

Intermittent backflushing with filtered Dl water was conducted as in Example 1 and permeate collected in a 50 liter jacketed vat.

Concentration of this permeate was begun even before completion of crossflow filtration in order to save time. Concentration and subsequent ultrafiltration of the concentrate was conducted on Millipore plate and frame tangential flow apparatus (Pellicon unit) equipped with two 100,000 NMW cut-off membrane cassette (10 square feet total area). Crystallization and harvesting was conducted as in Example I. 208 grams of purified enzyme was obtained having a specific activity of 22.8 U/mg.

This example demonstrates that the process of the present invention is suitable for large alcohol purification.

Example III

Alcohol Oxidase Activity

Alcohol oxidase (AO) activity measurements were based upon the determination of hydrogen peroxide product using horseradish peroxidase and a dye precursor, 2,2'-azino-di(3-ethyl-benzthiazolinesulfonic acid) (ABTS, Sigma). One unit of AO activity is defined as that amount of enzyme which will produce a μmole of hydrogen peroxide per minute at 25° C. and pH 7.5 AO assays were carried out on the day of sampling.

Total protein was determine using the bicinchoninic acid (BCA) assay. SDS polyacrylamide gel electrophoresis was conducted according to Laemmli, Nature, 227, 680 (1970), and showed an estimated 95% purity.

Example IV

Alcohol Oxidase (AO) Purity Analysis by Size Exclusion HPLC

Samples from 12 lots prepared similarly to the procedure set forth in Example I were analyzed by size exclusion HPLC and found to have an average purity of 96.8%.

A Toyo Soda. SW G4000 (600×7.5 mm) column and a TSK SW (75×7.5 mm) guard column (both from Biorad) was employed. The columns were equilibrated with at least two column volume (60 mls) of column buffer (0.1 M sodium phosphate, 0.1% sodium azide, pH 6.8) overnight at a flow rate of 0.1 ml/min or immediately before analysis at a flow rate of 1.0 ml/min. Column buffer and samples were filtered (0.44 um pore size) before use. The sample load ranged from 180-240 mg protein in a total volume of 3-10 ml. The flow rate was 1.0 ml/min. Proteins were eluted from this column in order of decreasing molecular weight. Proteins were detected by light absorbance at 280 nm and quantitated by integration of the peak areas.

That which is claimed is:

1. A process for the purification of alcohol oxidase from whole cells of *Pichia pastoris* grown on methanol comprising the steps of:
   (a) forming an aqueous suspension of from about 0.8 to about 6 volume percent of an autolytic treating agent, and a quantity of said whole cells of *Pichia pastoris* containing alcohol oxidase, wherein said cells are present in an amount in the range of from about 85 to about 150 grams per liter of said aqueous suspension, in a manner whereby said whole cells release at least a portion of said alcohol oxidase thereby forming aqueous liquor;
   (b) filtering said aqueous liquor by crossflow filtration to separate at least a portion of said alcohol oxidase from said aqueous liquor thereby forming an alcohol oxidase solution;
   (c) ultrafiltering and desalting said alcohol oxidase solution to form an alcohol oxidase suspension; and
   (d) recrystallizing alcohol oxidase from said alcohol oxidase suspension.

2. The process of claims 1 wherein the autolytic treating agent is selected from the group consisting of diethyl ether, methylene chloride, 1,2-dichloropropane, ethylidene chloride, chloroform, 2,2-dichloropropane, 1,1,1-trichloroethane, carbon tetrachloride, ethylene chloride, trichloroethylene, propylene chloride, 1,1,2-trichloroethane, tetrachloroethylene, trimethylene chloride, s-tetrachloroethane, 1,2,3-trichloropropane, pentachloroethane, and combinations of any two or more thereof.

3. The process o: claim 1 wherein the autolytic treating agent is chloroform.

4. The process o: claim 1 wherein the autolytic treating agent is methylene chloride.

5. The process of claim 1 wherein said autolytic treating agent is diethyl ether.

6. The process o: claim 1 wherein said crossflow filtration is performed with a microfilter having a pore size ranging from about 0.1 μm to about 5 μm.

7. The process of claim 6 wherein the crossflow filtration is performed at a superficial velocity of the aqueous liquor in the range of from about 5 feet per second to about 70 feet per second.

8. The process of claim 7 wherein the superficial velocity of the crossflow filtration is about 30 feet per second.

9. The process of claim 8 wherein said crossflow filtration is performed at a temperature in the range of from about 4° C. to about 20° C.

10. The process of claim 8 wherein said crossflow filtration is performed at a temperature in the range of from about 13° C. to about 15° C.

11. The process of claim 1 wherein ultrafiltration is performed utilizing a filter having a molecular weight cut-off ranging from about 10,000 MW to about 500,000 MW.

12. The process of claim 11 wherein ultrafiltration is performed utilizing a filter having a molecular weight cut-off of about 100,000 MW.

13. The process of claim 1 wherein the ultrafiltration is performed at a temperature in the range of from about 4° C. to about 20° C.

14. The process of claim 13 wherein the ultrafiltration is performed at a temperature of about 7° C.

15. The process of claim 1 wherein said desalting results in an end conductivity of said alcohol oxidase suspension ranging from about 500 μmho/cm to about 4,000 μmho/cm.

16. The process of claim 1 wherein said desalting results in an end conductivity of said alcohol oxidase suspension ranging from about 1900 μmho/cm to about 2500 μmho/cm.

17. The process of claim 1 wherein recrystallization is performed by adjusting the pH of the alcohol oxidase suspension to a value in the range of from about pH 6.0 to about pH 7.0.

18. The process of claim 17 wherein recrystallization is performed at pH 6.3.

19. A process for the purification of alcohol oxidase from whole cells of *Pichia pastoris* grown on methanol comprising the steps of:
   (a) forming an aqueous suspension of from about 0.8 to about 6 volume percent of an autolytic treating agent selected from the group consisting of diethyl ether, methylene chloride, 1,2-dichloroethylene, ethylidene chloride, chloroform, 2,2-dichloropropane, 1,1,1-trichloroethane, carbon tetrachloride, ethylene chloride, trichloroethylene, propylene chloride, 1,1,2-trichloroethane, tetrachloroethylene, trimethylene chloride, s-tetrachloroethane, 1,2,3-trichloropropane, pentachloroethane, and combinations of any two or more thereof, and a quantity o: said whole cells of *Pichia pastoris* containing alcohol oxidase, wherein said cells are present in an amount in the range of from about 85 to about 150 grams per liter of said aqueous suspension, in a manner whereby said whole cells release at least a portion of said alcohol oxidase thereby forming aqueous liquor;
   (b) filtering said aqueous liquor by crossflow filtration wherein said crossflow filtration is performed with a filter having a pore size ranging from about 0.1 μm to about 5 μm, at a superficial velocity of the aqueous liquor in the range of from about 5 feet per second to about 70 feet per second, and at a temperature ranging from about 4° C. to about 20° C., to separate at least a portion of said alcohol oxidase from said aqueous liquor thereby forming an alcohol oxidase solution;

(c) ultrafiltering and desalting said alcohol oxidase solution utilizing an ultrafilter having a molecular weight cut-off ranging from about 10,000 MW to about 500,000 MW performed at a temperature in the range of from about 4° C. to about 20° C. which results in a final conductivity of said alcohol oxidase solution ranging from about 500 μmho/cm to about 4,000 μmho/cm to form an alcohol oxidase suspension; and (d) recrystallizing alcohol oxidase from said alcohol oxidase suspension, wherein said recrystallization is performed at a pH ranging from about pH 6.0 to about pH 7.0.

* * * * *

UNITED STATES PATENT AND TRADEMARK OFFICE
CERTIFICATE OF CORRECTION

PATENT NO. : 4,956,290

DATED : September 11, 1990

INVENTOR(S) : Roger G. Harrison, Jr.
Lynn P. Nelles

It is certified that error appears in the above-identified patent and that said Letters Patent is hereby corrected as shown below:

In Claim 3, line 63, column 9, after the word "process" and before the word "claim", delete "o:" and insert therefor -- of --.

In Claim 4, line 65, column 9, after the word "process" and before the word "claim", delete "o:" and insert therefor -- of --.

In Claim 6, line 1, column 10, after the word "process" and before the word "claim", delete "o:" and insert therefor -- of --.

In Claim 19, line 57, column 10, after the word "quantity" and before the word "said, delete "o:" and insert therefor -- of --.

Signed and Sealed this

Fourteenth Day of January, 1992

Attest:

HARRY F. MANBECK, JR.

*Attesting Officer*     *Commissioner of Patents and Trademarks*